US000001943H

(19) United States

(12) Statutory Invention Registration

Kissinger et al.

(10) Reg. No.: US H1943 H

(43) Published: Feb. 6, 2001

(54) PROCESS FOR THE MANUFACTURE OF BISPHENOL-A

(75) Inventors: Gaylord M. Kissinger, Evansville, IN (US); Ryozo Sato, Murcia (ES)

(73) Assignee: General Electric Co., Pittsfield, MA (US)

(21) Appl. No.: 09/211,731

(22) Filed: Dec. 15, 1998

(51) Int. Cl.[7] ..... C07C 37/68

(52) U.S. Cl. ..... 568/724

(58) Field of Search ..... 568/724

(56) References Cited

U.S. PATENT DOCUMENTS

| | | | | |
|---|---|---|---|---|
| 3,621,664 | | 11/1971 | Saxer . | |
| 4,374,283 | * | 2/1983 | Aneja | 568/724 |
| 4,400,553 | * | 8/1983 | Aneja | 568/724 |
| 5,198,591 | * | 3/1993 | Kiedik | 568/724 |
| 5,214,073 | * | 5/1993 | Fukawa | 521/60 |
| 5,243,093 | | 9/1993 | Kissinger et al. . | |
| 5,315,042 | | 5/1994 | Cipullo et al. . | |
| 5,783,733 | * | 7/1998 | Kissinger | 568/724 |
| 5,786,522 | * | 7/1998 | Cipullo | 568/724 |

FOREIGN PATENT DOCUMENTS 246681 10/1987 (CS) .

* cited by examiner

*Primary Examiner*—Charles T. Jordan
*Assistant Examiner*—Aileen J. Baker

(57) ABSTRACT

A process for producing a dihydric phenol preferably bisphenol-A consisting of the steps of (1) formulating reaction ingredients of phenol, acetone, recycle bisphenol A, impurities, an acid catalyst and water, (2) reacting the ingredients to form a product mix consisting of bisphenol-A, unreacted phenol, by-products, acetone and water, (3) crystallizing the product mix forming a slurry of bisphenol-A/phenol adduct crystals solid phase, (4) separating the solid phase from the liquid phase by filtration, (5) removing the phenol from the bisphenol-A/phenol adduct to obtain a crude bisphenol-A, and (6) purifying the crude bisphenol by fractional melt crystallization to obtain a bisphenol-A of at least 99.5% purity. Optionally, the process may include the steps of recycling the liquid phase from step (3) back to the reaction step after removal of the water of reaction, and further removing entrained phenol and acetone from the removed water of reaction which phenol and acetone is also recycled back to the reaction step.

16 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR THE MANUFACTURE OF BISPHENOL-A

FIELD OF THE INVENTION

This invention relates to a novel process for producing bisphenol-A in a fully integrated commercial process. The process comprises five major steps with several optional minor steps. The fully integrated process provides a balance between process economics, environmental performance and product quality.

BACKGROUND OF THE INVENTION

Bisphenol-A has been an extremely useful chemical for many decades. As a difunctional monomer, it has been used in the preparation of numerous polymers. For example bisphenol-A [2,2-bis(4-hydroxyphenyl)-propane] has been utilized in preparing such materials as epoxy resins, polyetherimides, polyarylates and, in particular, polycarbonates. In certain of these polymer systems, particularly the epoxy systems, the purity of the bisphenol-A (hereinafter sometimes referred to as BPA) employed in the polymer reaction need not be that high. Epoxy resins only need BPA of approximately 95% purity. The impurity which is present in the greatest amount in such systems is generally orthopara BPA. However, with other polymer systems, particularly polycarbonates, the purity of the BPA must be substantially higher. Purities of BPA of about 99.50% or higher preferably 99.80 or 99.90% or higher are desirable and in many cases necessary for the preparation of BPA polycarbonates. The need for high purity BPA is particularly critical when it is used as a raw material in the melt process for the manufacture of polycarbonate. Not only is highly pure BPA required for use in this melt process, but also the differing types of impurities can have differing effects on the efficiency of the melt process and the performance characteristics of the polycarbonate made by the melt process. Therefore, there has been substantial attention directed to the preparation and purification of BPA.

The art is replete with references directed to the preparation of BPA. Usually this is done by the condensation of phenol with acetone in the presence of a catalyst system. Generally the catalyst is an acidic catalyst. For many years, one of the particularly useful catalyst systems in the patent art and employed commercially was hydrochloric acid. Although the economics of the process are initially good with respect to the conversion of the reactants to BPA, the maintenance of the apparatus is costly. The hydrochloric acid is extremely corrosive and ordinary metallic reactors and piping must be changed on a frequent basis. Obviously glass lined reactors or certain alloyed metals can be employed, however, these are quite expensive. In later years there seems to be the tendency to use a heterogeneous acidic catalyst system wherein the acidic catalyzation occurs at the catalyst surface and is actually bound to the catalyst. In this manner the "acid" does not flow with the unused reactants and BPA. Such catalyst systems are generally sulfonated polystyrenes which are substantially crosslinked such as the Amberlites and like materials.

After the BPA is prepared, various isolation and purification procedures are known. Many of these appear in the relatively voluminous patent art. Generally phenol is distilled off to a great extent and/or the initial purification by crystallization of a bisphenol-A phenol adduct. Distillation of the bisphenol-A itself can also be employed. The purification of the bisphenol-A phenol adduct can then be further accomplished through the addition of various organic solvents such as toluene or methylene chloride so as to remove the BPA from various impurities. Additionally water and various glycols such as ethylene glycol and glycerin have been used alone or together to separate and thus purify the BPA from its impurities.

SUMMARY OF THE INVENTION

In accordance with this invention, the novel process comprises five major steps to be utilized in a fully integrated commercial process for producing dihydric phenol, preferably Bisphenol-A. The process comprises the steps of (1) formulating of ingredients for reacting to form a product mixture comprising dihydric phenol, (2) reacting the ingredients forming a mixture comprising dihydric phenol, (3) subjecting the mixture to crystallization wherein a solid phase and a liquid phase are formed said solid phase is a crystal adduct of dihydric phenol and phenol, (4) removing phenol from the crystal dihydric phenol and phenol adduct, and (5) fractional melt crystallizing the product of step 4 to obtain highly purified dihydric phenol. Several optional minor steps may also be included in preferred embodiments of the process of this invention. These preferred embodiments additionally comprise some or all of the minor steps comprising (a) dehydrating the liquid phase from the crystallization step, which liquid phase is referred to as the mother liquor, (b) recovering phenol from a waste product of dehydration which is comprised of water and phenol wherein the phenol is recycled to the reaction step, (c) disposing of waste water from step (b) in accordance with environmental requirements and (d) recovering phenol from a purged portion of the dehydrated residue by way of catalytic tar cracking which purged portion comprises BPA, phenol and by-products.

DETAILED DESCRIPTION OF THE INVENTION

Figure 1:
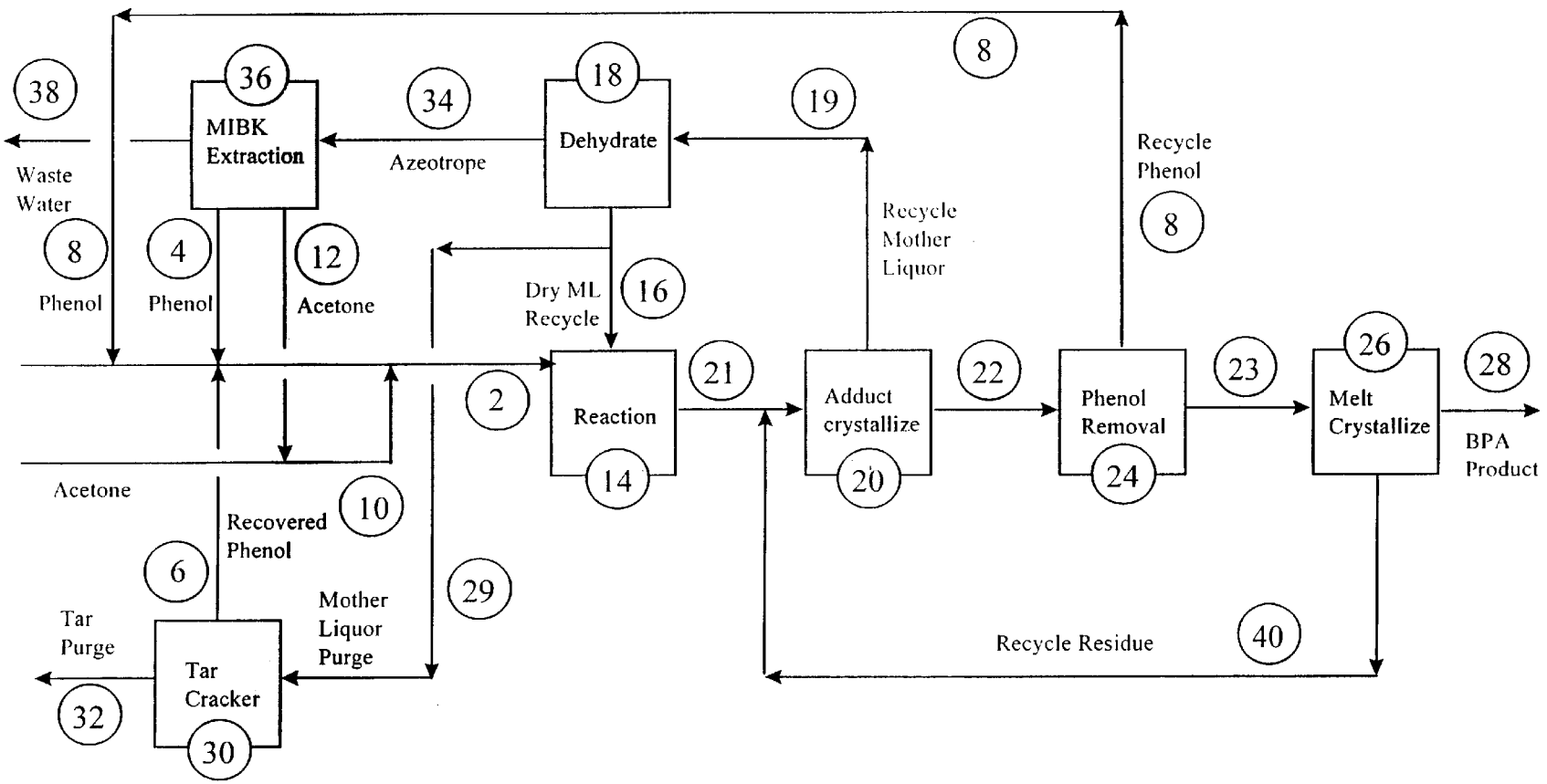
FIG. 1 is a flow diagram of a preferred embodiment of the novel process of this invention.

The novel feature of the process of this invention comprises five major steps as set forth above which process is utilized in an integrated commercial process for producing BPA and includes recovery of phenol from waste products of the process. A description of a preferred embodiment of the process follows.

First Step: Formulation

A reactor feed mix of ingredients is prepared for reaction of the ingredients to form a product mixture comprising a dihydric phenol, preferably bisphenol-A. The reactor feed mix is formulated from recycled dehydrated mother liquor comprising phenol and a dihydric phenol, preferably bisphenol-A, fresh phenol, a carbonyl compound, preferably acetone, recycle impurities and a mercaptan promoter such as, for example, 3-mercaptopropionic acid. The mother liquor is obtained from the separation of bisphenol-A and phenol adduct obtained from the crystallization step. Preferably, the mother liquor is essentially dehydrated by removal of water. These components form the reaction additives for reaction thereof and are continuously fed to the reactor step in controlled ratios for forming a bisphenol-A comprising mixture.

Second Step: Reaction

The formulation mixture of the First Step is reacted in the presence of a cationic ion exchange resin in the catalyzed condensation of phenol with acetone to form bisphenol-A. The reaction process utilizes "partial acetone conversion" so that the initial production of bisphenol-A is increased. More specifically, the reaction of phenol and acetone in the presence of an acidic catalyst under accelerated flow conditions or increased throughput so that the initial production of bisphenol-A is increased. The process employed in, and process conditions of, the "partial acetone conversion" reaction step is fully disclosed in U.S. Pat. No. 5,315,042, which is hereby incorporated herein by reference.

Briefly, the process comprises contacting phenol and acetone in the presence of an acidic catalyst at a relatively high effluent stream rate to promote an increase in initial production of BPA and a decrease in acetone conversion which is referred to in the patent as "partial acetone conversion". The BPA is then separated from the acetone in the effluent stream prior to depletion of the acetone and the separated acetone is then recycled. Acetone conversion decreases with increased flow rate while productivity increases dramatically. The effect is that higher productions of BPA may be achieved with increased flow through the same size vessel (or vessel size may be reduced while maintaining the same flow rate). The relative productivity increases for incremental increases in WHSV (weighted hourly space velocity). The % acetone conversion decreases for a corresponding increase in WHSV.

Third Step: Adduct Crystallization

The product mixture from reaction in the Second Step comprises BPA, unreacted phenol, unreacted carbonyl compound (acetone), water, and by products. The product mixture is fed to an adduct crystallizer wherein a slurry of BPA and phenol adduct crystals are formed. The crystallizer is generally operated at a temperature sufficient to cool the product mix to a temperature to form adduct crystals, preferably the temperature of the product mixture is brought to about 25° C. to about 90° C. The resulting slurry consists of a liquid phase and a solid crystal phase of a BPA and phenol adduct crystals. The slurry is separated into an adduct cake and a liquid component which liquid component is known as the mother liquor. Separation of the BPA/ phenol crystals into an adduct cake from the liquid phase may be achieved by filtration, centrifugation or other known solid/ liquid separation methods. One filtration method that may be utilized is employing rotary vacuum filters which may utilize liquid ring seal rotary vacuum pumps. The liquid seal employed may be a sodium hydroxide solution or liquid phenol, as disclosed in General Electric Company docket 8CL-7190 filed Sep. 16, 1998, Ser. No. 09/154,289 and assigned to the same assignee of record. Ser. No. 09/154,289 is hereby incorporated herein by reference. The recovered adduct cake, i.e. the adduct BPA/phenol cake is further processed in the Fourth Step below and the mother liquor is recycled as hereinafter described.

Fourth Step: Phenol Removal

The adduct cake from the Third Step is melted in order to remove phenol and recover BPA. The recovery of BPA may be by feeding the adduct melt to a vacuum distillation column equipped with a vacuum source and operated at an elevated temperature in order to vaporize phenol at the operating temperature and vacuum of the distillation column leaving BPA as a melt. Alternatively, the melt may be fed to a packed bed inert gas stripper wherein an inert gas such as nitrogen is passed counter-current to the melted adduct cake. The adduct cake is heated to a temperature sufficient to form phenol vapor. The nitrogen desorbs the phenol vapor leaving a BPA melt essentially free of phenol. Other processes for recovery of phenol may be by such methods utilizing a thin film evaporator.

Fifth Step: Fractional Melt Crystallization

Following the removal of phenol in the Fourth Step from the crude BPA/phenol adduct, the BPA residue is purified to a high degree in this Fifth Step of the process. The fractional melt crystallization process is disclosed in U.S. Pat. No. 5,243,093 which is hereby incorporated herein by reference. Briefly, the process is directed to purifying impure bisphenol-A by fractional crystallization in a falling film dynamic crystallizer. In this step of the process of this invention, crystalline bisphenol-A purity of at least about 99.50%, preferably at least 99.80% or 99.90% may be obtained.

The composition in its melt form is now subjected to fractional melt crystallization, usually multi-stage melt crystallization. The temperature is lowered gradually until the temperature is somewhat below the melting point of the desired substance, in this case bisphenol-A, MP156.7C. In some cases the composition may have to be heated above the melting temperature of the desired substance and then brought down below the freezing point. Clearly this particular procedure is advantageous in separating the desired component of a composition from impurities. Ideally, the desired component crystallizes onto the surface of the vessel holding the melt composition. The theory of the fractional melt crystallization is that the desired component preferentially is crystallized out from the melt while the undesired impurities remain in their liquid state or are entrapped in the crystalline medium to a limited extent. In a multiple stage fractional melt crystallization, the desired component purity of the crystalline medium is upgraded in each successive stage through the phases of crystallization, partial melting, and total melting. A preferred apparatus to carry out the fractional melt crystallization is referred to as the "Sulzer" melt crystallization apparatus. This is a falling film dynamic crystallizer, which may be obtained from Sulzer Canada, Inc., a subsidiary of Sulzer Brothers, Ltd., Switzerland, or other equipment manufacturers. An example of such an apparatus obtained from Sulzer Canada and general multi-stage fractional melt crystallization procedure is disclosed in detail in U.S. Pat. No. 3,621,664 issued to K. Saxer and is incorporated herein by reference. This type of crystallizer is substantially different from a singe stage, static state crystallizer, for example, as shown in Konecny Czech patent publication 246681 wherein bisphenol-A is purified in a static crystallizer. The preferred embodiment of the invention utilizes a "Sulzer" apparatus and the continued detailed explanation of the invention is now disclosed with respect to that type of apparatus.

A crude bisphenol-A stream from which about 90% or more of the unreacted phenol as well as essentially all of the unreacted acetone and water is removed. The remaining components of the stream comprise products of the side reactions. The major component is usually o,p' bisphenol-A. The crude bisphenol-A stream is fed to a fractional melt crystallization apparatus, preferably utilizing falling films. This apparatus generally comprises a group of tubes with central distribution system to each tube, a liquid circulation system for both the heat exchange medium and the bisphenol-A containing melts, a circulation pump, a collecting tank at the bottom of the tubes, a feed tank for each stage which also functions as a holding tank for residue from crystallization phase and a partial melt phase liquor, the process being conducted in multiple stages with three phases in each stage—a crystallization phase; a partial melting phase and a melt phase. Each successive stage produces a purer form of the bisphenol-A, the number of stages being sufficient to obtain the desired final purity in high yields and thereby finishing one complete cycle.

The combination of the fourth and fifth steps of the present inventive process removes the impurities in the BPA that are particularly troublesome in obtaining high performance polycarbonate from the melt polymerization process before the BPA is fed to the melt polycarbonate process. The fourth step prepares a single adduct and the fifth step removes the critical undesirable impurities without the use of solvents. The array of impurities removed in the fourth and fifth steps differ from the array of impurities removed by the prior art double adduct crystallization processes.

Unlike the conventional interfacial process which employs solvents and carriers which remove the undesirable impurities present in the BPA feed stock during the polymerization process before the finished polycarbonate is produced, the melt polymerization does not employ such solvents and carriers. Therefore, any undesirable impurities present in the BPA when fed to the polycarbonate melt polymerization process will remain in the finished polycarbonate produced by the melt polymerization process.

By the process of the present invention, the BPA produced is particularly low in these undesirable byproducts and polycarbonate made by the melt process from this BPA is particularly suited for demanding high performance applications such as optical disks, such as video disks and compact disks as well as electronic equipment components and high quality optical devices and lenses. Even more surprising is that this is accomplished in an environmentally prudent manner since melt crystallization employs no solvents.

Minor Steps

The minor steps employed in preferred embodiments of this process, which are optional in the full scope of the invention, comprise dehydration of the mother liquor by extraction of waste water, which may also contain some phenol to be disposed of in accordance with environmental requirements and wherein a small portion of the dehydrated stream is subjected to tar cracking for phenol recovery. Briefly, the mother liquor from the adduct crystallization step is first dehydrated and then recycled back to the formulation step. The process purge is taken as a minor portion from the dehydrated stream and is sent to a tar cracking step for recovery of phenol. The bottom residue, namely "tar", is sold or disposed by other means in accordance with environmental requirements.

In the dehydration step, water of reaction, unreacted acetone, and some phenol is removed from the recycled mother liquor. A bottom stream from this step is recycled to the formulation step. An overhead stream referred to as the azeotrope which may have as much as 10% phenol in water, but may also contain acetone, is processed in a methyl isobutyl ketone extraction unit. In this unit, phenol and acetone are recovered and recycled back to the formulation step. The waste water of reaction and process waste water are disposed of in accordance with environmental requirements. One particular waste water treatment is to purify the waste water for discharge into a site waste water treating plant.

In the tar cracking process, an amount of dehydrated recycled mother liquor is purged from the process to maintain an equilibrium level of color and impurities. This amount typically will be from about 2 to about 15%, of the recycled stream. A catalyst, which may be a strong base, such as sodium hydroxide, may be utilized along with heat to yield phenol. The phenol is recovered as an overhead product from a distillation column and recycled to the formulation step. The bottoms residue, tar, is sold or disposed of in accordance with environmental requirements.

DETAILED DESCRIPTION OF THE DRAWING

Formulation mix stream 2 consisting of phenol from streams 4, 6, and 8 and acetone from acetone stream 10 which also contains acetone from stream 12 and essentially dehydrated mother liquor stream 16 from dehydration unit 18 are fed to reactor 14 for reaction of the formulation mix for a product mix comprising BPA and other products of the reaction. The reaction product mix is then fed to adduct crystallizer unit 20 through stream 21 wherein a slurry of crystals of BPA and phenol are formed and separated into a solid crystal phase of BPA and phenol and a liquid phase (mother liquor). The solid crystal phase 22 from adduct crystallizer unit 20 is fed to a phenol removal unit 24 wherein phenol recovered from unit 24 is recycled back through stream 8 to formulation mix stream 2, or may, alternatvely, in whole or in part, be used to wash the adduct cake in the filtration step. The residue from the phenol removal unit 24 is sent to fractional melt crystallizer unit 26 through stream 23 from which highly purified BPA 28 is obtained. The mother liquor phase from the adduct crystallizer unit 20 is fed to dehydration unit 18 through stream 19 wherein a substantial portion of the dehydrated mother liquor is returned to the reactor unit 14 through stream 16. A mother liquor purge stream 29 is fed to a tar cracker unit 30 wherein phenol is recovered in stream 6 and fed to formulation mix stream 2. Tar residue 32 is obtained from tar cracker 30 and disposed. An azeotrope portion 34 from dehydration unit 18 is fed to MIBK (methyl isobutyl ketone) extraction unit 36 wherein phenol stream 4 and acetone stream 12 are recovered and returned to formulation mix stream 2. Waste water stream 38 is removed and disposed. Recycle residue stream 40 from melt crystallizer unit 26 is recycled back to adduct crystallizer unit 20 through reactor product mix stream 21 from reactor unit 14.

The composition and absorbancy of selected streams in the process of the present invention as well as selectivity and conversion was determined by multiple analyses at various points in the process. The results of these analyses are shown in Tables 1 through 8. The points in the process as shown in FIG. 1 are tabulated below:

| TABLE | STREAM NUMBER |
|---|---|
| 1 | 2 |
| 2 | 21 |
| 3 | 16 |
| 4 | 19 |
| 5 | 22 |
| 6 | 23 |
| 7 | 40 |
| 8 | 28 |

In the headings of the tables the following abbreviations are used and have the meanings shown below:

| ABBREVIATION | MEANING |
|---|---|
| PNL | % phenol |
| IPP | % isopropenyl phenol |
| PPBPA | % para-para-bisphenol A |
| OPBPA | % ortho-para-bisphenol A |
| DIMER | % dimers |
| CHRM | % chroman I |
| SPIRO | % spirobiindane |
| BPX-1 | % trisphenols - group 1 |

-continued

| ABBREVIATION | MEANING |
|---|---|
| BPX-2 | % trisphenols - group 2 |
| UNK | % unknowns |
| PUR | BPA/BPA + impurities in % |
| IMPUR | % total impurities |
| % ACE | % acetone |
| H2O | % water |

-continued

| ABBREVIATION | MEANING |
|---|---|
| SH | ppm thiol content |
| SEL | selectivity |
| CONV | % conversion |
| IA | initial absorbance at 350 nm in methanol solution (UV range) |
| TF | absorbance at 350 nm in methanol solution (UV range) |
| OLI | % oligomers |

Closed Loop Process Analytical Data

R220A Inlet [1]

| | PNL | IPP | PPBPA | OPBPA | DIMER | BPX1 | CHRM | SPIRO | BPX2 | UNK | PUR | IMPUR | % ACE | H2O | SH |
|---|---|---|---|---|---|---|---|---|---|---|---|---|---|---|---|
| Number Points | 91 | 91 | 91 | 91 | 91 | 91 | 91 | 91 | 91 | 91 | 85 | 91 | 93 | 93 | 92 |
| Mean | 81.367 | 0.000 | 10.622 | 2.935 | 1.388 | 0.804 | 0.693 | 0.124 | 0.183 | 1.875 | 56.916 | 8.011 | 4.00 | 0.09 | 375 |
| Minimum Point | 77.853 | 0.000 | 9.031 | 2.535 | 1.151 | 0.683 | 0.558 | 0.075 | 0.072 | 1.488 | 52.944 | 6.781 | 3.53 | 0.02 | 284 |
| Maximum Point | 84.188 | 0.000 | 14.596 | 3.248 | 1.563 | 0.987 | 0.801 | 0.166 | 0.374 | 2.446 | 66.237 | 9.114 | 4.92 | 0.62 | 452 |
| Range | 6.335 | 0.000 | 5.565 | 0.713 | 0.412 | 0.304 | 0.243 | 0.091 | 0.302 | 0.958 | 13.293 | 2.333 | 1.39 | 0.60 | 168 |

R220A Outlet [2]

| | PNL | IPP | PPBPA | OPBPA | DIMER | BPX1 | CHRM | SPIRO | BPX2 |
|---|---|---|---|---|---|---|---|---|---|
| Number Points | 90 | 90 | 90 | 90 | 90 | 90 | 90 | 90 | 90 |
| Mean | 67.002 | 0.001 | 24.627 | 3.082 | 1.443 | 0.832 | 0.714 | 0.130 | 0.199 |
| Minimum Point | 63.422 | 0.000 | 18.026 | 2.122 | 0.950 | 0.552 | 0.046 | 0.084 | 0.067 |
| Maximum Point | 76.509 | 0.018 | 27.638 | 3.336 | 1.672 | 0.982 | 0.826 | 0.189 | 0.381 |
| Range | 13.087 | 0.018 | 9.612 | 1.214 | 0.722 | 0.430 | 0.780 | 0.105 | 0.314 |

R220A Outlet Part II [2]

| | UNK | % ACE | H2O | OLI | TF | SEL | IMPUR | PUR | CONV |
|---|---|---|---|---|---|---|---|---|---|
| Number Points | 90 | 93 | 93 | 29 | 31 | 31 | 90 | 84 | 93 |
| Mean | 1.958 | 0.31 | 1.19 | 0.3 | 4.2 | 0.9586 | 8.371 | 74.583 | 92.58 |
| Minimum Point | 1.208 | 0.03 | 0.87 | 0.0 | 3.4 | 0.9052 | 5.465 | 71.136 | 87.98 |
| Maximum Point | 2.704 | 1.01 | 1.50 | 9.0 | 5.1 | 0.9913 | 9.478 | 76.946 | 99.26 |
| Range | 1.496 | 0.98 | 0.63 | 9.0 | 1.6 | 0.0861 | 4.013 | 5.810 | 11.28 |

C211B [3]

| | H2O | PNL | IPP | PPBPA | OPBPA | DIMER | BPX1 | CHRM | SPIRO | BPX2 | UNK |
|---|---|---|---|---|---|---|---|---|---|---|---|
| Number Points | 61 | 61 | 61 | 61 | 61 | 61 | 61 | 61 | 61 | 61 | 61 |
| Mean | 0.067 | 80.064 | 0.002 | 10.940 | 3.215 | 1.543 | 0.975 | 0.826 | 0.126 | 0.241 | 2.069 |
| Minimum Point | 0.030 | 77.617 | 0.000 | 9.689 | 2.670 | 0.477 | 0.807 | 0.620 | 0.106 | 0.171 | 1.763 |
| Maximum Point | 0.200 | 81.918 | 0.026 | 13.837 | 3.645 | 1.803 | 1.697 | 1.032 | 0.146 | 0.352 | 3.108 |
| Range | 0.170 | 4.301 | 0.026 | 4.148 | 0.975 | 1.326 | 0.890 | 0.412 | 0.040 | 0.181 | 1.345 |

V224 [4]

| | H2O | TF | PNL | IPP | PPBPA | OPBPA | DIMER | BPX1 | CHRM | SPIRO | BPX2 | UNK |
|---|---|---|---|---|---|---|---|---|---|---|---|---|
| Number Points | 31 | 29 | 30 | 30 | 30 | 30 | 30 | 30 | 30 | 30 | 30 | 30 |
| Mean | 0.892 | 4.4 | 80.848 | 0.000 | 10.447 | 3.103 | 1.479 | 0.961 | 0.808 | 0.118 | 0.235 | 2.001 |
| Minimum Point | 0.070 | 3.8 | 78.500 | 0.000 | 9.105 | 2.777 | 0.486 | 0.824 | 0.623 | 0.000 | 0.159 | 1.634 |
| Maximum Point | 1.470 | 4.8 | 82.656 | 0.003 | 13.366 | 3.418 | 1.705 | 1.755 | 0.995 | 0.141 | 0.352 | 3.437 |
| Range | 1.400 | 1.0 | 4.156 | 0.003 | 4.261 | 0.641 | 1.219 | 0.931 | 0.372 | 0.141 | 0.193 | 1.803 |

-continued

Closed Loop Process Analytical Data

V226F [5]

| | PNL | IPP | PPBPA | OPBPA | DIMER | BPX1 | CHRM | SPIRO | BPX2 | UNK |
|---|---|---|---|---|---|---|---|---|---|---|
| Number Points | 55 | 55 | 55 | 55 | 55 | 55 | 55 | 55 | 55 | 55 |
| Mean | 41.790 | 0.000 | 57.905 | 0.181 | 0.018 | 0.045 | 0.007 | 0.002 | 0.038 | 0.013 |
| Minimum Point | 35.052 | 0.000 | 47.045 | 0.121 | 0.000 | 0.000 | 0.000 | 0.000 | 0.000 | 0.000 |
| Maximum Point | 52.448 | 0.000 | 64.675 | 0.338 | 0.127 | 0.103 | 0.068 | 0.064 | 0.090 | 0.100 |
| Range | 17.396 | 0.000 | 17.630 | 0.217 | 0.127 | 0.103 | 0.068 | 0.064 | 0.090 | 0.100 |

V226B [6]

| | TF | PNL | IPP | PPBPA | OPBPA | DIMER | BPX1 | CHRM | SPIRO | BPX2 | UNK |
|---|---|---|---|---|---|---|---|---|---|---|---|
| Number Points | 59 | 60 | 60 | 60 | 60 | 60 | 60 | 60 | 60 | 60 | 60 |
| Mean | 0.5 | 0.028 | 0.020 | 99.492 | 0.235 | 0.058 | 0.053 | 0.027 | 0.003 | 0.063 | 0.021 |
| Minimum Point | 0.2 | 0.002 | 0.008 | 98.251 | 0.153 | 0.024 | 0.025 | 0.008 | 0.001 | 0.051 | 0.012 |
| Maximum Point | 1.6 | 0.055 | 0.053 | 99.697 | 0.792 | 0.322 | 0.226 | 0.151 | 0.016 | 0.117 | 0.079 |
| Range | 1.4 | 0.047 | 0.044 | 1.445 | 0.639 | 0.298 | 0.201 | 0.143 | 0.016 | 0.066 | 0.067 |

V262 [7]

| | PNL | IPP | PPBPA | OPBPA | DIMER | BPX1 | CHRM | SPIRO | BPX2 | UNK |
|---|---|---|---|---|---|---|---|---|---|---|
| Number Points | 27 | 27 | 27 | 27 | 27 | 27 | 27 | 27 | 27 | 27 |
| Mean | 1.303 | 0.202 | 95.261 | 1.048 | 0.450 | 1.095 | 0.199 | 0.021 | 0.283 | 0.138 |
| Minimum Point | 0.000 | 0.000 | 88.385 | 0.582 | 0.000 | 0.565 | 0.000 | 0.000 | 0.164 | 0.001 |
| Maximum Point | 9.495 | 0.257 | 97.983 | 2.423 | 1.116 | 1.706 | 0.573 | 0.056 | 0.649 | 0.296 |
| Range | 9.495 | 0.257 | 9.598 | 1.840 | 1.116 | 1.141 | 0.573 | 0.056 | 0.485 | 0.295 |

V277 [8]

| | IA | PNL | IPP | PPBPA | OPBPA | DIMER | BPX1 | CHRM | SPIRO | BPX2 | UNK |
|---|---|---|---|---|---|---|---|---|---|---|---|
| Number Points | 27 | 27 | 27 | 27 | 27 | 27 | 27 | 27 | 27 | 27 | 27 |
| Mean | 0.122 | 0.007 | 0.005 | 99.909 | 0.039 | 0.010 | 0.013 | 0.003 | 0.001 | 0.007 | 0.006 |
| Minimum Point | 0.078 | 0.003 | 0.002 | 99.765 | 0.023 | 0.003 | 0.005 | 0.001 | 0.000 | 0.004 | 0.003 |
| Maximum Point | 0.208 | 0.034 | 0.027 | 99.949 | 0.073 | 0.030 | 0.037 | 0.008 | 0.002 | 0.018 | 0.012 |
| Range | 0.130 | 0.032 | 0.025 | 0.184 | 0.050 | 0.027 | 0.032 | 0.007 | 0.002 | 0.014 | 0.009 |

DESCRIPTION OF EXAMPLE

A detailed example of one run of the process of this invention utilizing FIG. 1 is as follows:

Formulation mix (stream 2) consisting of:

81.3% phenol 4.0% acetone 14.6% impurities 4.0% impurities 10.6% BPA 0.1% $H_2O$ Reaction product mix from the reactor to adduct crystallizer 67.0% phenol 24.6% para-para-bisphenol-A 8.4% ortho-para -bisphenol-A, dimer, water, tar, etc.

Recycle mother liquor from adduct crystallizer feed to dehydration unit 20

80.8% phenol 10.4% p,p'BPA 8.8% tar, other by products, o,p'BPA, dimer, etc.

Adduct crystallizer cake 5 from adduct crystallizer to phenol removal unit 30

41.8% phenol 57.9% PPBPA 0.3% other by products and impurities

BPA from phenol removal unit 30 sent to fractional melt crystallizer unit 26 consists of 99.5% para-para bisphenol-A 0.5% impurities BPA from fractional melt crystallizer unit 26 consists of 99.9% PPBPA 0.1% impurities Recycle residue from fractional melt crystallizer to adduct crystallizer unit consists of 95.3% PPBPA 1.3% phenol 3.4% impurities It may become apparent to those skilled in the art that various changes and modifications may be made herein without departing from the invention and it is intended in the appended claims to cover such changes and modifications as fall within the true spirit and scope of the invention.

What is claimed is:

1. A process for preparing a dihydric phenol comprising the steps of (1) formulating the reactor ingredients for forming a dihydric phenol, (2) reacting the ingredients to form a product mixture comprising dihydric phenol, unreacted phenol, carbonyl compound and water, (3) subjecting the product mixture to crystallization wherein a slurry is formed comprising a mother liquor phase and a solid phase, said solid phase is an adduct of dihydric phenol and phenol, (4) separating the solid dihydric phenol and phenol phase from the liquid phase, (5) extracting the phenol from the solid dihydric phenol and phenol phase to obtain a crude dihydric phenol, and (6) purifying the crude dihydric phenol by fractional melt crystallization to obtain a dihydric phenol of at least about 95% purity.

2. The process of claim 1 wherein the dihydric phenol is bisphenol-A

3. The process of claim 1 wherein the promoter is a mecaptan.

4. The process of claim 1 wherein the mother liquor from the crystallizing step is dehydrated to remove water of reaction, a portion of unreacted carbonyl compound and a portion of phenol.

5. The process of claim 4 wherein the dehydrated mother liquor is recycled to the formulating reactor.

6. The process of claim 4 wherein the process consists essentially of the additional steps of (a) extracting entrained phenol and carbonyl compound from the water of reaction, (b) recycling the extracted phenol and carbonyl compound to the reaction step, and (c) disposing of the reaction waste water.

7. The process of claim 4 wherein the carbonyl compound is acetone.

8. A process for preparing polycarbonate of high purity comprising preparing bisphenol A by the process of claim 2, melting the bisphenol A, mixing the molten bisphenol A with diphenyl carbonate, reacting the molten bisphenol A with the diphenyl carbonate.

9. A process for making an article comprising preparing a high purity polycarbonate by the process of claim 8 and forming the polycarbonate prepared into the article.

10. The process of claim 9 wherein the article is formed by injection molding.

11. An article made by the process of claim 10 wherein the article is an optical disk.

12. An article made by the process of claim 10 wherein the article is an electronic component.

13. An article made by the process of claim 10 wherein the article is a lens.

14. The process of claim 9 wherein the article is formed by extrusion.

15. The process of claim 10 wherein the article is formed by vacuum forming.

16. The process of claim 1 wherein the reaction ingredients comprise phenol, acetone and a promoter.

* * * * *